Sept. 13, 1955 R. E. SHEPHERD Plant Pat. 1,419
ROSE PLANT
Filed May 28, 1954
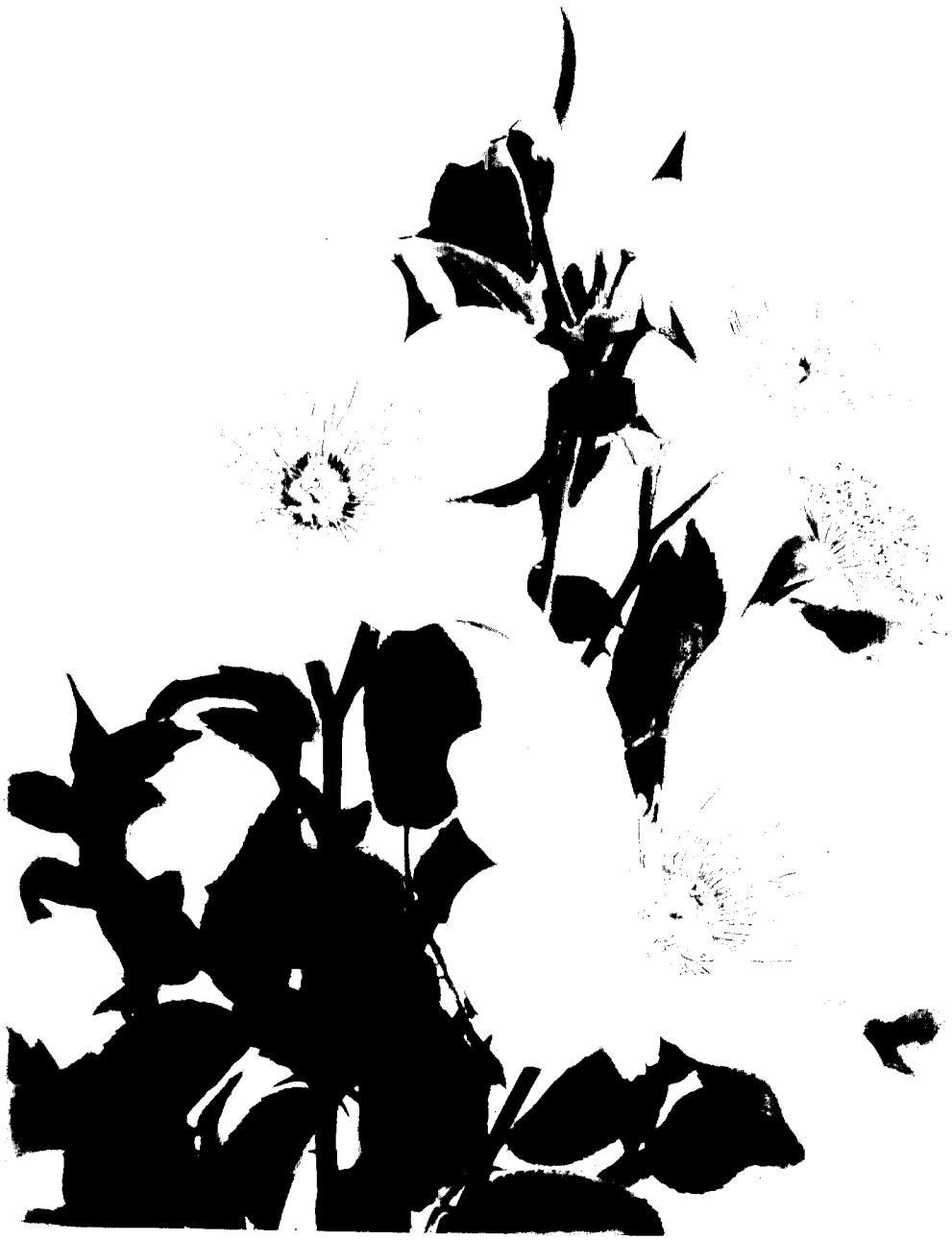
INVENTOR
Roy E. Shepherd Jr
By Orville M Kile
Plant Patent Agt.

United States Patent Office

Plant Pat. 1,419
Patented Sept. 13, 1955

1,419

ROSE PLANT

Roy E. Shepherd, Medina, Ohio, assignor to Edith C. Bosley, Mentor, Ohio

Application May 28, 1954, Serial No. 433,320

1 Claim. (Cl. 47—61)

My present invention pertains to a new type of shrub rose which combines the everblooming qualities of the hybrid tea with extreme winter hardiness. It blooms continuously from spring to fall and shows no winter injury at 20 degrees below zero.

My new variety is the result of a cross made by me at my nurseries in Medina, between the unpatented varieties Soeur Therese and *R. spinosissima*. It has been reproduced at the same location by means of budding, and its characteristics appear to be permanent.

Accompanying illustrations show in approximately true colors, an opening bud, three open flowers and portion of an older flower from which the petals have dropped showing the stamens and calyx. Also shown attached to these specimens are portions of the stems and foliage.

In the following detailed description of my new variety, color plate numbers refer to Ridgway's Color Standards and Nomenclature.

THE PLANT

Growth habit: Vigorous; branching; height to 4 feet.
Hardiness: Hardy even to 20 degrees below zero.
Blooming habit: Very free bloomer throughout the summer.
Canes: Heavy; rigid; russet tinged.
Stems: Slender; medium green, not shown in Ridgway's but approximating Forest Green (Pl. XVII).
Thorns: Many; sharp; long and slender; downward-pointing; often red-tinged.
Peduncle: Short (approximately 1½ inches long); thickly covered with fine spines which are usually reddish or russet-tinged.
Foliage: Pinnately compound, usually with 5 leaflets.
*Quantity.*—Plentiful.
*Texture.*—Light but substantial.
*Size.*—Overall measurements average 6 by 4½ inches. Terminal leaflet measures approximately 2½ inches long and 1½ inches wide.
*Shape.*—Broad oval with rounded base and acute apex which is sometimes curved sidewise. Edge finely serrated.
*Color.*—Medium green, between Cress Green and Dark Cress Green (Pl. XXXI) on upper surface; approximately Light Elm Green (Pl. XVII) on under surface. Sometimes red-tinged below.
*Aspect.*—Dull. Midrid prominent.
*Rachis.*—Slender; deeply grooved on upper surface; occasional spine on under surface.
*Stipules.*—Long and relatively large; clinging except for sharp points.

FLOWER

Bud:
*Size.*—Large for single flower. Approximately 1¼ inches long and ½ inch broad at base, just before beginning to spread.
*Form.*—Before showing color the bud is short and conical.
*Color.*—Strontian Yellow (Pl. XVI), blending into lighter tones of Citron Yellow (Pl. XVI).
*Opening.*—Rapid.
*Sepals.*—Simple; long-pointed; reflex early.

Bloom:
*Borne.*—Singly and in clusters.
*General color effect.*—Clear yellow, somewhat darker at base of petals, with prominent red and yellow center.
*Form.*—Single, open saucer with large and prominent center, formed by pistils and stamens.
*Size.*—Large, 4 to 5 inches in diameter under normal conditions.
*Petalage.*—Five petals.

Petals:
*Size.*—Length 1½ to 2¼ inches by width of 1½ to 2 inches at top of petal. Lower portion of petal is narrower.
*Shape.*—Obovate; cupped; edges convolute.
*Color.*—Young bloom is Citron Yellow (Pl. XVI), blending into Barium Yellow, with Strontian Yellow in the center. Older bloom is Amber Yellow (Pl. XVI), with Wax Yellow at base, and Baryta Yellow (Pl. IV) at the edges. Occasionally there appear small splotches of pink at the top of one or two petals—usually in the fall flowers.
*Arrangement.*—Petals overlap at base.
*Texture.*—Medium thickness.
*Behavior.*—Drop cleanly.
*Fragrance.*—Slight spicy fragrance.
*Keeping qualities.*—Extremely good for a single rose.

Reproductive organs:
*Pistils.*—Tightly bunched in center of flower. Styles—short; Light Viridine Yellow (Pl. IV) tinged with red. Stigmas—small; Citron Green (Pl. XXXI).
*Stamens.*—Many, surrounding pistils. The stamens and pistils form a beautiful and showy center for the flower, the stamens extending almost half the length of the petals. Filaments—long, bringing anthers far beyond pistils; of uneven lengths and usually cupped or curved inward; Nopal Red (Pl. I), blending into Peach Red. Anthers—large. Apricot Yellow, blended with Pinard Yellow (both Pl. IV).
*Ovaries.*—Cress Green (Pl. XXXI).

Having thus disclosed my invention, I claim:

The new and distinct variety of shrub rose plant, substantially as herein shown and described, characterized particularly by its everblooming habit; its extreme winter hardiness; its vigorous growth; and its clear yellow single bloom with prominent center.

No references cited.